United States Patent [19]

Infante

[11] 4,046,732

[45] Sept. 6, 1977

[54] DISPERSANT FOR THE APPLICATION OF DENTAL CERAMIC

[76] Inventor: Samuel J. Infante, 1 Rosedale Terrace, Livingston, N.J. 07039

[21] Appl. No.: 539,916

[22] Filed: Jan. 9, 1975

[51] Int. Cl.$^2$ ............................. C08J 5/02; C08J 5/10; C08J 5/32; C08J 33/12
[52] U.S. Cl. ................................. 260/31.2 R; 32/2; 32/8; 32/12; 32/15; 260/32.4; 260/33.8 UA; 260/DIG. 36
[58] Field of Search ........................... 32/8, 15, 12, 2; 106/35; 260/DIG. 36, 31.2 R, 32.4, 33.8 UA

[56] References Cited

U.S. PATENT DOCUMENTS

| 2,013,295 | 9/1935 | Tidd | 32/2 |
| 2,347,567 | 4/1944 | Kresse | 32/12 |
| 2,558,139 | 6/1951 | Knock et al. | 260/DIG. 36 |
| 2,980,998 | 4/1961 | Coleman et al. | 32/12 |

FOREIGN PATENT DOCUMENTS

| 1,129,575 | 5/1962 | Germany | 260/DIG. 36 |

Primary Examiner—Allan Lieberman
Attorney, Agent, or Firm—Carella, Bain, Gilfillan & Rhodes

[57] ABSTRACT

Dispersants for the application of both a ceramic opaque underlay to a substrate and gingival and incisal porcelains thereover and methods for fabricating dental prostheses therewith in which the first dispersant consists essentially of methyl methacrylate polymer, methyl methacrylate monomer, ethyl acetate, trichloroethane and nitroethane in selected relative proportions which form an easily applicable dispersion with dental ceramic opaque for application to dental prosthetic substrates, the dispersion rapidly setting under relatively low temperatures to produce a mechanically strong, substantially water insoluble opaque mask compatible with but insoluable in aqueous-based gingival and incisal dental porcelains applied thereover to fabricate the finished surface of a dental prosthesis; and in which the second dispersant for the gingival and incisal porcelain consists essentially of an aqueous solution of a styrene, butyl acrylate-acrylic acid terpolymer neutralized with ammonia and a styrene-methyl methacrylate methacrylic acid terpolymer neutralized with ammonia; the dispersion rapidly setting under relatively low temperatures of an infra red lamp such that it can be ground or that touch-up porcelain may be applied without damaging the first application.

1 Claim, No Drawings

DISPERSANT FOR THE APPLICATION OF DENTAL CERAMIC

BACKGROUND OF THE INVENTION

A dental prosthesis is fabricated by the application of a dental, ceramic opaque to a prosthetic substrate, usually platinum. The ceramic opaque is adapted to mask the dark color of the platinum substrate. Additionally, it forms an underlying layer which is adapted to receive an overlay of both a gingival and an incisal porcelain to form the finished dental prosthesis. While the gingival and incisal porcelains are of slightly different color as are the gingival and incisal enamels on a natural tooth, they are also somewhat translucent. Thus, it is essential that the underlying ceramic opaque completely mask the dark platinum substrate.

Presently, dental ceramic opaque is mixed with water to a light, workable consistency and painted upon the substrate. The water-based ceramic covers so poorly that usually several applications are necessary. However, when water is employed as the dispersant, subsequent applications erode and damage the underlying previous applications. Thus, it is frequently necessary to fire the ceramic opaque at high temperatures on the order of 1800° F. before employing additional ceramic opaque. Each firing requires from 1.5 to 2.5 hours.

Gingival and incisal porcelain are also presently dispersed in water. Thus, it is absolutely necessary to fire the ceramic opaque after a satisfactory mask has been achieved, so that it will not dissolve, drift or otherwise be impaired under the influence of the water from the gingival and incisal porcelains.

Usually, the application of ceramic opaque to achieve a satisfactory mask requires 2 or 3 firings of 1.5 to 2.5 hours each resulting in a bisque sufficiently strong to receive water dispersed gingival and incisal porcelains. As a result, as much as 6.5 hours of firing time is consumed merely to achieve a proper mask of the platinum substrate by means of the ceramic opaque.

Thereafter, the gingival and incisal porcelains must be applied on top of the bisque of underlying ceramic opaque. The gingival and incisal porcelains are presently dispersed in water to a consistency which permits application to the ceramic opaque bisque. The water tends to evaporate rapidly with the porcelains returning to a powdery state which has very low mechanical strength. Therefore, it is extremely difficult to shape the tooth with the incisal and gingival porcelains because the working time is so short. Nevertheless, when the gingival and incisal porcelains are applied and shaped, the prosthesis is again fired until the gingival and incisal porcelains have fused. The fired prosthesis is now ready for finishing, carving and shaping by means of diamond stones and the like. After final shaping and fitting, a last firing is employed at somewhat higher temperatures than employed for the first firing so as to achieve a glazed surface.

Thus, in the current procedure, the prosthesis is fired four or five times, each firing requiring 1.5 to 2.5 hours. This is extremely tedious and time-consuming. Additionally, it is extremely difficult to shape the gingival and incisal porcelains when mixed with water by reason of their rapid drying and return to a powdery state.

It is among the objects and advantages of the present invention to provide a dispersant for the underlying ceramic opaque on dental prostheses and the like which will dry sufficiently rapidly under the relatively low temperatures of an infra red lamp to permit the addition of still more ceramic opaque, two, three, four or as many times as are necessary in order to insure complete masking of the substrate without resort to high temperature firing each time additional ceramic opaque is applied.

Another object of the invention is to provide a second dispersant for gingival and incisal porcelains which dries sufficiently rapidly under the relatively low temperatures of an infra red lamp so as to be easily carved without resort to high temperature firing thereby reducing high temperature, time consuming firings for the application of gingival and incisal porcelains to a single end firing for glazing.

Yet another object of the present invention is to provide first and second dispersants as aforesaid which are mutually compatible such that the ceramic opaque underlying layer need not be fired to a bisque prior to the application of gingival and incisal ceramic without danger of damage to the ceramic opaque mask over the substrate.

Still another object of the invention is to provide a dispersant for the application of ceramic opaque which is sufficiently resistant to water erosion when dried for a short time under an infra red lamp to accept water-based gingival and incisal porcelains without significant impairment.

SUMMARY OF INVENTION

A dispersant for the application of ceramic opaque to a substrate consisting by volume essentially of approximately 1.0 part polymethylmethacrylate, 0.5 to 4.5 parts monomethylmethacrylate, 1.0 to 4.5 parts ethylacetate, 1.0 to 4.5 parts trichlorethane and 10.0 to 25.0 parts nitroethane.

A dispersant for application of gingival and incisal porcelains to a ceramic opaque masked substrate consisting essentially of an aqueous solution of styrene-butyl acrylate, acrylic acid terpolymer neutralized with ammonia and styrene-methyl methacrylate methacrylic acid terpolymer neutralized with ammonia.

A method for masking a substrate with ceramic opaque comprising adding ceramic opsque to a dispersant consisting by volume essentially of one part polymethylmethacrylate, 0.5 to 4.5 parts monomethylmethacrylate, 1.0 to 4.5 parts ethylacetate, 1.0 to 4.5 parts trichloroethane and 10.0 to 25.0 parts nitroethane in quanttities sufficient to achieve a desired viscosity and applying the ceramic opaque containing dispersant to a substrate to effect at least a partial mask and setting the dispersant by the application of relatively low temperature heat.

A method for applying gingival or incisal porcelains to a ceramic opaque masked substrate comprising adding porcelain to an aqueous solution of a styrene-butyl acetate, acrylic acid terpolymer neutralized with ammonia and styrene-methyl methacrylate, methacrylic acid terpolymer neutralized with ammonia in quantities sufficient to achieve a desired viscosity, applying the porcelain containing dispersant to a ceramic opaque masked substrate and setting the dispersant by the application of relatively low temperature heat until sufficiently hard to be shaped.

PREFERRED EMBODIMENT OF INVENTION

The objects and advantages aforesaid as well as other objects and advantages may be achieved by the compositions and methods hereinafter set forth.

The present invention contemplates the use of a first dispersant for the application of ceramic opaque to the substrate which sets up relatively rapidly under relatively low temperatures sufficient to receive additional ceramic opaque without disturbing the underlying layer so as to achieve a complete mask without firing at relatively high temperatures to a bisque.

The dispersant comprises the following constituents:

TABLE I

| CONSTITUENT | MINIMUM VOLUME (ml) | PREFERRED VOLUME (ml) | MAXIMUM VOLUME (ml) |
|---|---|---|---|
| polymethyl methacrylate | 1.0 | 1.5 | 1.5 |
| monomethyl methacrylate | 0.5 | 1.0 | 4.5 |
| ethyl acetate | 1.0 | 1.0 | 4.5 |
| trichloroethane | 1.0 | 1.0 | 4.5 |
| nitroethane | 10.00 | 15.00 | 25.00 |

In the preparation of the mask for the substrate, powdered ceramic opaque is mixed with a dispersant which may be formulated in accordance with Table I above. A thin mix of the powdered ceramic opaque is made with the dispersant to achieve a consistency which may be brushed onto the substrate. A first layer is applied and then dried under the relatively low temperatures of infra red lamp in an open room for approximately 10 to 15 minutes whereupon the dispersant sets up sufficiently hard that it can be touched up by the application of additional ceramic opaque containing dispersant without damage to the underlying layer. It has been found that the above dispersant when mixed with ceramic opaque has more than 50% better masking effectiveness than ceramic opaque dispersed in water. The procedure may be employed as set forth above any number of times necessary to insure a complete mask of the substrate without the danger of disturbing previous applications. At no time is the ceramic opaque fired to a bisque prior to the application of gingival and incisal porcelain which would require heating in a closed furnace to temperatures on the order of 1800° F.

The gingival and incisal porcelains may be applied by use of another dispersant or by the use of ordinary water. If water is employed as the dispersant, the underlying layer of ceramic opaque, set up with the heat from an infra red lamp in an open room, is sufficiently waterproof not to be significantly eroded by the water in which the gingival and incisal porcelains are dispersed.

However, it has been found that the use of another polymer-based dispersant for the gingival and incisal porcelains avoids many of the problems of their application and shaping. This second dispersant is compatible with the first dispersant employed for the application of the ceramic opaque and will not erode it during application. As in the case of the dispersant for the ceramic opaque, the second dispersant rapidly sets up in an open room at the relatively low temperatures generated by an infra red lamp to a sufficient hardness that it may be easily shaped, carved or ground without crumbling.

The second dispersant is comprised of about 63% by weight water, about 22.2% by weight of a styrene-butyl acrylate acrylic acid terpolymer neutralized by ammonia and about 14.8% by weight of a styrene-methyl methacrylate methacrylic terpolymer neutralized with ammonia. The second dispersant is preferably diluted with water in amounts of approximately 6 parts by volume water to one part by volume dispersant, although a range from five to eight parts by volume water to one part by volume dispersants is acceptable.

The gingival or incisal porcelains are dispersed in the second dispersant to form a workable mixture which is applied over the set-up ceramic opaque. The incisal and gingival porcelains can be shaped as applied without drying to a powdery mask. Additionally, it rapidly dries with the use of an infra red lamp in an open room and thereafter may be easily carved or ground to achieve the desired shape.

After an acceptable shape of the gingival and incisal portions of the prosthesis has been achieved, a first firing is employed at approximately 1800° F. This results in a bisque which may be ground, or touched up with additional incisal or gingival porcelains to achieve the final shape. If the prosthesis is touched up with additional gingival or incisal porcelains dispersed in the second dispersant, it tenaciously adheres to the bisque and again quickly sets up for shaping, grinding or carving under an infra red lamp in an open room.

After the final shape has been achieved, the prosthesis is given the second and final firing at approximately 1840° F. to produce a glazed surface. Thereafter, the prosthesis is polished in the usual manner.

Thus, by use of the two above-mentioned dispersants, a dental prosthesis may be prepared with but two high temperature firings, the firing of the gingival and incisal porcelains to form a bisque for final shaping and the second firing to achieve a surface glaze. As many as three or four additional firings, each consuming 1.5 to 2.5 hours are eliminated. Additionally, it is much easier to mask the substrate with ceramic opaque and to shape the prosthesis with both the gingival and incisal porcelains. More importantly, as in the case of all porcelains or ceramics, each high-temperature firing in a furnace involves the danger of thermal shock damage both on the heating cycle and on the cooling cycle. The elimination of firings reduces by that number of times the chance of such damage.

With respect to the first mentioned dispersant, it has been found that the poly and mono methacrylates must be employed. Other polymers have been tested but found wanting in various ways. For instance, vinyls require such a long period of time to set-up before the gingival and incisal porcelains can be applied to the opaque that there is little saving in overall time. If the vinyl has not set up before the gingival and incisal overlays are applied, the opaque can be disturbed.

The styrenes have been found to be too viscous and difficult to apply. The acetates either dry too fast, providing too little working time or are too viscous. The ureas may be applied with relative ease and set up within a reasonable period of time; however, the ureas tend to delaminate from the metal substrate on high temperature firing.

With respect to the relative quantities of the constituents of the first above-named dispersant, if too much of any of the mono methacrylate, trichloroethane, ethyl acetate, or nitroethane is employed, the viscosity of the dispersant is sufficiently reduced that there is incomplete masking. With respect to any or all of the above ingredients, if too little are employed with respect to the poly methyl methacrylate, the viscosity of the dispersion becomes so high that it is unworkable and the set-up time is too rapid.

It will be understood by those skilled in the art that many modifications and variations of the present invention are possible without departing from the spirit and the scope thereof.

What is claimed is:

1. A dispersant for the application of ceramic opaque to a substrate consisting by volume essentially of a. 1.0 parts polymethylmethacrylate,
b. 0.5 to 4.5 parts monomethylmethacrylate,
c. 1.0 to 4.5 parts ethylacetate,
d. 1.0 to 4.5 parts trichloroethane, and
e. 10.0 to 25.0 parts nitroethane.

* * * * *